United States Patent [19]

Tabler et al.

[11] 4,129,605
[45] Dec. 12, 1978

[54] RECOVERING STYRENE BY COMPLEXING WITH COPPER(I) SULFONATES

[75] Inventors: Donald C. Tabler; Marvin M. Johnson, both of Bartlesville, Okla.

[73] Assignee: Phillips Petroleum Company, Bartlesville, Okla.

[21] Appl. No.: 763,460

[22] Filed: Jan. 28, 1977

[51] Int. Cl.$^2$ .................. C07C 15/10; C07C 7/08
[52] U.S. Cl. ................................... 260/669 A; 203/51
[58] Field of Search ........ 260/669 A, 669 QZ, 674 A; 203/29, 38, 57

[56] References Cited

U.S. PATENT DOCUMENTS

| | | | |
|---|---|---|---|
| 2,399,514 | 4/1946 | Smoker | 260/669 A |
| 2,823,243 | 2/1958 | Robinson | 260/669 A |
| 3,356,593 | 12/1967 | Suzuki | 260/674 A |
| 3,634,530 | 1/1972 | Bills | 260/669 A |
| 3,684,665 | 8/1972 | Abe et al. | 203/9 |
| 3,763,015 | 10/1973 | Morimoto et al. | 203/29 |
| 4,031,153 | 6/1977 | Haskell | 260/669 A |

Primary Examiner—Delbert E. Gantz
Assistant Examiner—Joseph A. Boska

[57] ABSTRACT

Styrene is recovered from a styrene-rich stream by complexing with a copper(I) sulfonate. The complex is treated to displace the styrene from the complex.

24 Claims, 2 Drawing Figures

RECOVERING STYRENE BY COMPLEXING WITH COPPER(I) SULFONATES

FIELD OF THE INVENTION

The invention relates to the recovery of styrene.

BACKGROUND OF THE INVENTION

Styrene is a valuable chemical, particularly as a monomer in the preparation of resinous polymers such as polystyrenes, or in the preparation of rubbery compounds such as butadiene/styrene copolymers. Increasing monomer costs, increasing demands for polymeric substances made from styrene, have pushed the search for new and economical sources of styrene.

One potential and intriguing source of styrene lies in the fact that processes such as naphtha cracking result in a mixed effluent which contains styrene as a minor component. Such streams can be separated, such as by fractional distillation, to produce a primarily $C_8$ stream containing some styrene, along with a motley collection of diolefins, acetylenics, and the like. These unsaturates, diolefins and acetylenics, can be hydrogenated, and the resulting hydrogenated streams then can be again fractionally distilled to obtain a styrene-rich stream. All this is very fine, except that this styrene-rich stream, while a tantalizingly close source of styrene monomer, yet, heretofore, has not been subject to an economical method of getting the styrene out.

SUMMARY OF THE INVENTION

We have discovered a method of neatly and conveniently extracting styrene from such a styrene-rich stream. According to our process, styrene is complexed with a copper(I) sulfonate. The complex is treated to displace the styrene, and the styrene is readily recovered in quite pure form. The copper(I) sulfonate can be recycled for efficient operation.

Figure 1:
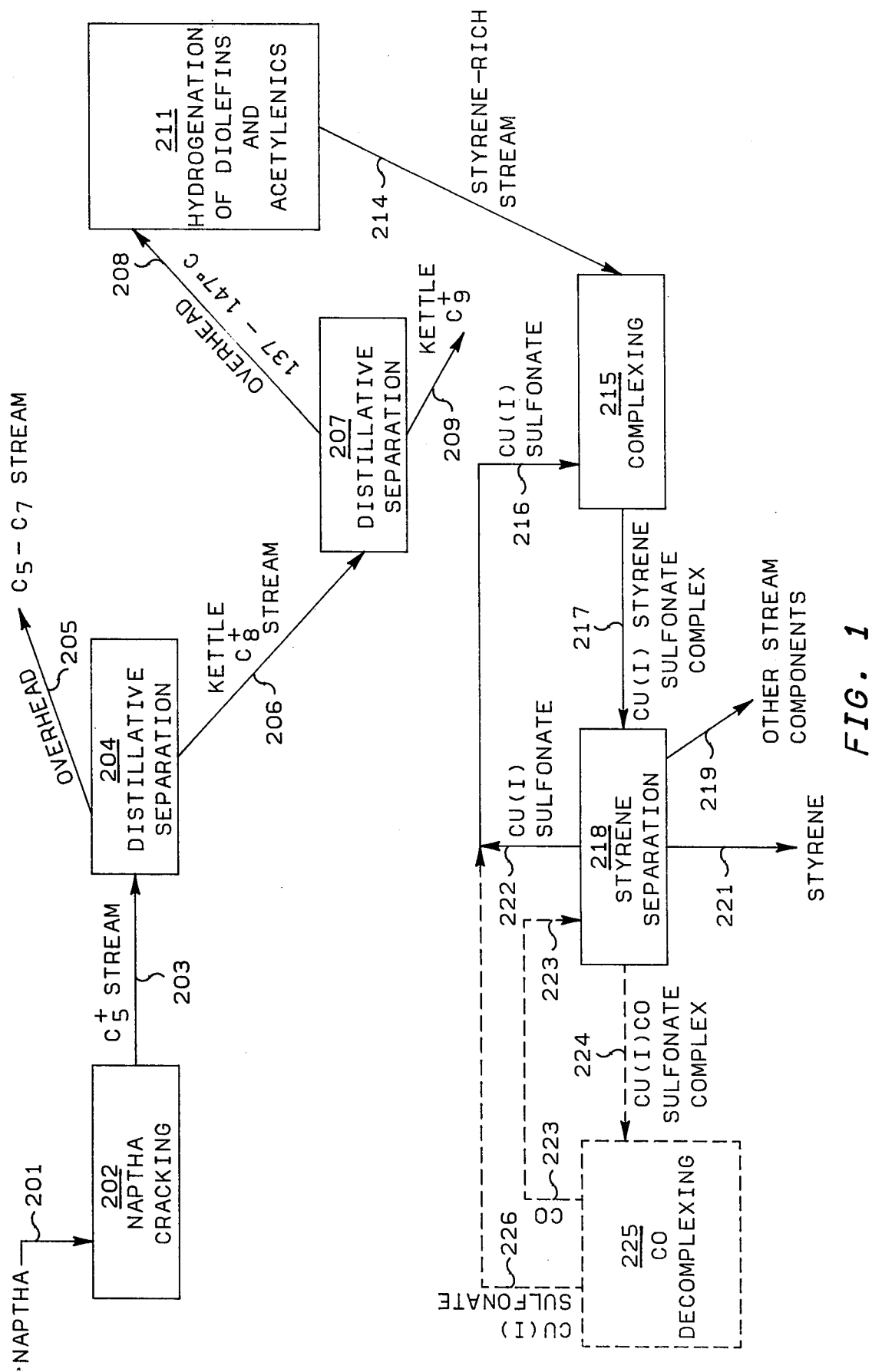
FIG. 1 is a schematic showing one application of our process to a naphtha stream. Naphtha 201 is cracked 202, and a $C_5^+$ stream 203 recovered. The $C_5^+$ stream 203 is separated 204 to recover overhead a $C_5$–$C_7$ stream 205 for use elsewhere, and a kettle $C_8^+$ stream 206 containing styrene. The $C_8^+$ stream 206 is fractionally distilled to recover stream 208 containing styrene boiling between about 137°–147° C., and a kettle product 209 of $C_9^+$. The heavy kettle stream 209 can be used elsewhere in the modern oil and refining and chemicals complex frequently termed a petrocomplex. The styrene-containing fraction 208 is hydrogenated 211 to convert therein contained diolefins and acetylenics into more saturated compounds such as monoolefins.

Optionally, though this generally is unnecessary, the hydrogen-treated styrene-rich fraction 214 can be separated (not shown), such as by fractional distillation to remove some of the more saturated compounds prior to contacting 215 with the copper(I) sulfonate 216.

The hydrogen-treated styrene-rich fraction 214 is contacted 215 with a copper(I) sulfonate 216 as complexing agent to form a copper(I)(styrene) sulfonate complex containing stream 217. The complex-containing stream 217 is treated 218 to separate out other stream components 219, to recover the styrene 221, and to recover for recycle the copper(I) sulfonate 222. Shown in dashed line is an optional mode whereby carbon monoxide 223 is used to displace 218 the styrene in the complex, resulting in a copper(I)(CO) sulfonate 224 and a styrene stream 221. The copper(I)(CO) sulfonate complex 224 is treated 225 to release the CO 223 for recycle, and to recover the copper(I) sulfonate 226 for reuse.

Figure 2:
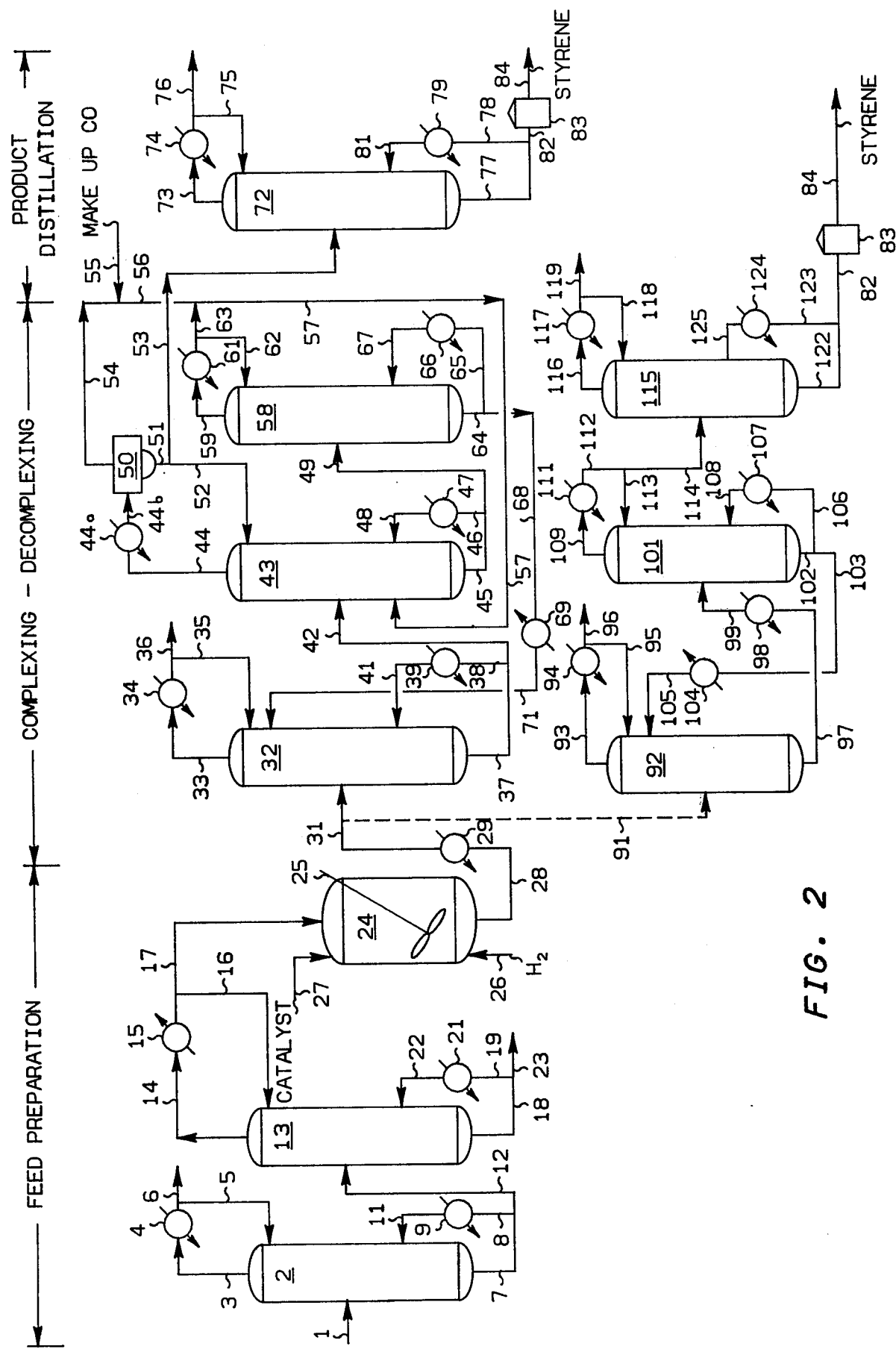

In FIG. 2, a pyrolysis gasoline 1 is fractionated 2 and 13 to obtain a $C_8^+$ fraction 17. The $C_8^+$ fraction is hydrogenated 24, and then contacted 32 with the complexing agent copper(I) sulfonate. The stream 42 containing complexed styrene is contacted with carbon monoxide 43 which is one means of displacing the styrene from the complex. Further separation 58 and 72 recovers the styrene 83, while carbon monoxide is recycled 54, 56, 57.

Alternatively, after the hydrogenation step 24, the hydrogenated stream 91 can be treated 92 with copper(I) sulfonate to complex the styrene, and the complexed styrene 97 can be decomplexed thermally 101, and separated 115 to recover the styrene 83.

FIG. 2 is discussed in more detail hereinafter.

DETAILED DESCRIPTION OF THE INVENTION

According to our process, styrene can be recovered from a styrene-rich stream comprising styrene and other close boiling hydrocarbons by complexing the styrene with a copper(I) sulfonate; separating the complex; and then decomplexing to recover the styrene.

In accordance with one aspect of the process of our invention, a $C_8^+$ stream can be treated so as to ultimately obtain from it the included styrene. Such a $C_8$ stream can be obtained from a variety of sources within an integrated refining complex.

For example, a $C_5^+$ stream comprising styrene admixed with various hydrocarbons including aromatic hydrocarbons, benzene, toluene, xylenes, and higher, unsaturated compounds such as the lower olefins, acetylenics such as phenylacetylene, and the like, can be obtained as a by-product stream resulting from the cracking, either thermal or catalytic, of naphtha, gas-oil, and the like, typically at temperatures above such as about 700° C., which cracking results in a variety of light olefins also including ethylene, propylene, butenes. The light olefins can be readily fractionated off to be separated as monomers for various purposes, polymerization, and the like. The $C_5^+$ by-product stream, divorced of the light olefins, can be conventionally fractionated to obtain an overhead stream comprising saturated and unsaturated hydrocarbons of about 5 to 7 carbon atoms per molecule, containing most of the benzene, toluene, cyclohexane, methylcyclohexane, and the like. The kettle product from such a fractionation contains most of the $C_8$ and higher molecular weight compounds.

A similar $C_8^+$ stream also can be derived from a naphtha cracking process, and will also contain desirable amounts of styrene.

Such $C_8^+$ streams comprising styrene and other hydrocarbons such as xylene isomers and ethylbenzene plus the $C_9$ and $C_{10}$ aromatics preferably is fractionated to obtain a relatively narrow boiling fraction between about 137° and 147° C. This fraction contains styrene together with other close boiling aromatic hydrocarbons, particularly o-xylenes, as well as the other xylene isomers, diolefins of 8 to 9 carbon atoms, olefins such as octenes, nonenes, and octadienes, paraffins such as octanes, naphthenes, and acetylenes such as phenylacetylene. The residual $C_9^+$ kettle stream can be further conventionally treated in the petrocomplex for recovery of valuable components.

The preferred narrow boiling 137°–147° C. fraction preferably is selectively hydrogenated to convert diolefins and acetylenics into more saturated compounds, such as olefins, phenylacetylene to styrene, and the like. Various methods of hydrogenation of such unsaturates are known. One typical process employs a palladium catalyst supported on a carrier, such as calcium carbonate or alumina, and partially deactivated by adding metals such as lead, copper, zinc, bismuth, mercury, tin, or cadmium. Palladium concentration on the carrier should preferably be in the range of about 0.01 to 10 weight percent, preferably about 0.1 to 5 weight percent. The catalyst can be employed in the form of pellets, powders, or other suitable form known to the art. Typical operating conditions for such hydrogenations include pressures in the range of about 1 to 20 kg/cm$^2$, temperature in the range of about 30° C. to 100° C., employing an LHSV (liquid hourly space velocity) of about 5 to 50.

The hydrogenated fraction is treated in accordance with the further steps of our invention, employing a copper(I) sulfonate as a solution in an aromatic hydrocarbon solvent, thereby forming a complex of copper(I) sulfonate/styrene. Preferably, this is conducted under distillative contacting conditions so that noncomplexed components are separated and removed, and a stream of copper(I) styrene sulfonate complex in aromatic hydrocarbon is recovered. The solution containing the complexed styrene then is thermally decomposed to a temperature to release the styrene, and separate the copper(I) sulfonate aromatic hydrocarbon solution for recycle. Alternatively, the complex can be subjected to a displacement by contacting with carbon monoxide at relatively low temperatures to form a copper(I) sulfonate/carbon monoxide complex, with release of styrene which can be readily separated. The copper(I) sulfonate/carbon monoxide complex then can be subjected to decomposition by treatment at elevated temperatures to release the carbon monoxide, for recycle and reuse, and separation of the copper sulfonate aromatic hydrocarbon solution for recycle and reuse.

Copper(I) Sulfonates

The copper(I) sulfonates employed in the process of our invention are selected from:
(a) the copper(I) salt of an alkane sulfonic acid of 4 to 20 carbon atoms per molecule;
(b) the copper(I) salt of an aromatic sulfonic acid including hydroxy aromatic and haloaromatic sulfonic acids of 6 to 22 carbon atoms per molecule;
(c) the copper(I) salt of a petroleum sulfonic acid.

Among the alkane sulfonic acids employed in the practice of our invention are the straight as well as branched chain alkane sulfonic acids, including as exemplary species n-butane sulfonic acid, 2-ethyl-1-hexane sulfonic acid, 2-methylnonane sulfonic acid, dodecane sulfonic acid, 2-ethyl-5-n-octyldecane sulfonic acid, n-eicosane sulfonic acid, and the like, alone or in admixture. Among these presently preferred is 2-ethyl-1-hexane sulfonic acid because of the favorable solubility of the copper(I) sulfonate in the aromatic solvent.

The aromatic, including hydroxy aromatic and haloaromatic, sulfonic acids employable in the practice of our invention typically include such as benzene sulfonic acid, the alkylbenzene sulfonic acids wherein the alkyl constituent contains 1 to 16 carbon atoms such as p-toluene sulfonic acid, p-dodecylbenzene sulfonic acid, p-hexadecylbenzene sulfonic acid, and the like; naphthalene sulfonic acids, phenol sulfonic acid, naphthol sulfonic acids; the halobenzene sulfonic acids such as p-chlorobenzene sulfonic acid, p-bromobenzene sulfonic acid; and the like, alone or in admixture. A presently preferred aromatic sulfonic acid is p-dodecylbenzene sulfonic acid because of its commercial availability and hence economy, and also since it results in a copper(I) sulfonate which produces a relatively low viscosity solution in the aromatic solvent and hence is easier to handle.

Commercially available mixtures of aromatic sulfonic acids such as o-, m-, and p-dodecylbenzene sulfonic acids, can be employed. Such admixtures will generally predominate in the para isomer, such as about 85 to 90 mol percent, because of probable steric considerations. The commercial acid is suitable for preparation of the copper(I) dodecylbenzene sulfonates.

The petroleum sulfonic acids employable in the context of our invention can be prepared from a deasphalted, solvent-refined, petroleum fraction exhibiting a viscosity of about 140 to 720 SUS (210° F.). A presently preferred sulfonation stock is a propane-fractionated, solvent-extracted, dewaxed, Mid-Continent oil of about 200–230 SUS exhibiting a viscosity index of about 90 to 100 or higher. Such a Mid-Continent oil is defined as a mixed base or intermediate base oil as described in 1 *The Science of Petroleum* 7 (Oxford University Press, London, 1938). Such an oil can be sulfonated, typically, with a 10 percent SO$_3$-90 percent SO$_2$ mixture in a continuous operation as described in U.S. Pat. No. 3,135,693 to Whitney et al. Using an SO$_3$:oil weight ratio of about 0.08, and a reaction temperature of about 115°, at a reaction time of about 5 minutes including mixing and soaking intervals. Such a treatment system is operated in the liquid phase at pressures of about 100–120 psig. Effluent from the reaction is subjected to a two-stage flash for SO$_3$-SO$_2$ removal or to recover the sulfonated product.

The copper(I) sulfonate compositions employed thereafter are prepared from any of the sulfonic acids as described above by contacting a sulfonic acid with cuprous oxide. Such contacting preferably employs a solution of the sulfonic acid in a diluent, contacting with the cuprous oxide, preferably with the provision for removing the consequent water of reaction, such as in a Dean-Stark trap, employing an oxygen-free inert atmosphere, such as under nitrogen, employing a molar ratio of acid to copper which can vary broadly, such as about 0.5 to about 2.5, preferably as reasonably close to 1 as convenient. Preparation employs sufficient time to produce substantially complete reaction. When excess cuprous oxide is employed, in the preparation, the surplus is separated from the reaction mixture by filtration and the like. When excess sulfonic acid is employed, care must be taken to separate or neutralize as much free acid as feasible to avoid corrosion of equipment in the subsequent complexing-decomplexing steps. The resulting copper(I) sulfonate can be separated from the diluent by removal of the diluent by such as vacuum distillation. However, where an aromatic hydrocarbon diluent is employed, said separation is unnecessary, since the contacting of the styrene-containing stream conveniently employs the copper(I) sulfonate and an inert aromatic hydrocarbon diluent.

In preparing the copper(I) sulfonates, any normally liquid saturated aliphatic, saturated cycloaliphatic, or aromatic hydrocarbon can be employed, typically including n-hexane, n-octane, cyclohexane, benzene, toluene, any of the xylenes, various other alkylbenzenes such as ethylbenzene, halogenated hydrocarbons such as chloroform, chlorobenzene, and other solvents including such as ethylene glycol ethers, such as ethylene glycol monoethyl ether, tetramethylsulfone, and the like. Preferred diluents are the aromatic hydrocarbons, such as toluene and xylene, because of greater solubility of the copper(I) sulfonates, thus allowing more copper to be available for complexing with the styrene and carbon monoxide in the process.

As a practical matter, it is desirable to employ the copper(I) sulfonate as a solution, with as high a concentration of the sulfonate salt as possible, since this increases the economy in the styrene-extracting step, since the greater will be the complexing capacity of the system. The copper(I) salts typically are employed in any suitable broad ratio such as about 0.2 to 2.5 molar solution, preferably about 0.5 to 2, more preferably about 0.7 to 1.5, because such solutions have viscosities readily handled by conventional means and sufficient copper is available for subsequent complexing with the styrene and CO.

The solution employed should be as the copper(I) sulfonate salt dissolved in a hydrocarbon solvent wherein the hydrocarbon solvent exhibits a boiling point higher than that of styrene, thus higher than 145° C. (at atmospheric pressure), in order subsequently that the styrene can be stripped off conveniently without losing solvent. Suitable hydrocarbons include the aromatic hydrocarbons such as the alkylbenzenes of suitable boiling points such as n-propylbenzene, sec-butylbenzene, amylbenzenes, as well as commercial mixtures of normally liquid alkylbenzenes having a suitable boiling range. It also is convenient and suitable to prepare the copper(I) sulfonate salt itself in the aromatic hydrocarbon solvent which is to be employed in the styrene contacting step.

Styrene Contacting Step

The styrene contacting step can be conducted in any suitable absorber zone or absorber means by which the styrene-containing stream can be intimately contacted with the copper(I) sulfonate aromatic liquid solution. Although the contacting can be conducted at a wide range of pressures, such as 40 to 7600 mm Hg (5.3–1013 kPa), preferably it is conducted below atmospheric pressure, such as about 65 to 700 mm Hg (8.7–93 kPa), at a temperature of about 0° C. to 120° C., preferably about 20° C. to 100° C., in a tray-type contacting device, for a suitable and convenient time, exemplarily about ¼ minute to 5 minutes since the rate of complexing is very high. This particular type of apparatus operated at the above-mentioned conditions makes it practical to combine the complexing step with distillation overhead of the noncomplexed material. This is because the relatively low contacting temperature allows the copper(I) styrene sulfonate to form, while the relatively low pressure allows the noncomplexed material to distill overhead at this low temperature. The overhead stream is then treated conventionally for recovery of valuable components.

Of course, other modes of separation of the complexed material can be employed, if desired.

The solution containing the copper(I) sulfonate/styrene complex in the aromatic hydrocarbon then is treated for release and recovery of the styrene.

Recovery of Styrene

Recovery of the styrene is accomplished by a decomplexing mode. The copper(I) sulfonate/styrene complex can be decomplexed (decomposed) by heat treatment, or by displacement.

According to the heat decomplexing mode, the copper(I) sulfonate/styrene complex aromatic hydrocarbon solution is heated at pressures and temperatures suitable to decompose the complex and free the styrene. Suitable temperatures range widely so long as they are not high enough to cause rapid polymerization of styrene. An exemplary range is such as about 120° C. to 200° C., presently preferably about 150° C. to 190° C., employing pressures of about 130 to 1100 mm Hg (17.3 to 146.6 kPa), preferably about 320 to 890 mm Hg (42.6 to 118.6 kPa), for a suitable time, exemplarily about ¼ minute to 5 minutes. The styrene is taken off as a vapor phase.

In an alternate mode, one that is presently more preferred, because lower temperatures which are less likely to cause polymerization of the styrene can be employed, the copper(I) sulfonate/styrene complex in the aromatic hydrocarbon is treated with carbon monoxide. The carbon monoxide is complexed preferentially by the copper(I) sulfonate. According to this aspect of our process, the carbon monoxide can be employed exemplarily over a range of about 1 mole CO/mole Cu(I) to 2 moles CO/mole Cu(I), employing a suitable temperature of such as about 0° to 110° C., presently preferred about 20° to 100° C.; a suitable pressure such as about 20 to 1500 mm Hg, presently preferred about 65 to 760 mm Hg; for a suitable time such as about ¼ minute to 5 minutes. The carbon monoxide is intimately contacted with the styrene complex in any suitable absorber means, displacing the styrene which then is removed as gas phase, leaving a copper(I) sulfonate/carbon monoxide complex dissolved in the aromatic hydrocarbon solvent.

The gas phase from either mode, primarily styrene with some aromatic hydrocarbon in the first mode, or styrene with some aromatic hydrocarbon and some carbon monoxide in the second mode, then can be treated such as by fractionation to recover a pure styrene stream useful for such as a monomer in preparation of various resins or rubbers.

In the first mode, the copper(I) sulfonate salt in the aromatic hydrocarbon can be readily recycled for further styrene complexing.

According to the second mode, however, the copper(I) sulfonate/carbon monoxide in aromatic hydrocarbon stream requires further treatment in order to be reused. The carbon monoxide copper sulfonate complex is passed to a decomplexing means wherein the carbon monoxide is readily liberated by heating the mixture to an effective decomplexing temperature, such as about 10° C. below the boiling point of the aromatic solvent up to about the boiling point thereof, preferably such as about the boiling point for convenience in reboiling. This desorption can be carried out at pressures of such as about 20 to 2300 mm Hg, preferably about 380 to 1500 mm Hg. The carbon monoxide stripped off and any aromatic solvent boiling off can be recycled and reemployed according to the second mode above. The copper(I) sulfonate aromatic hydrocarbon solution can be recycled for further styrene contacting.

Where desired, an inhibitor such as p-t-butyl catechol can be added to the styrene stream to avoid polymerization thereof.

Thus, in accordance with our process, styrene can be obtained readily and effectively. A typical prior art process of recovering styrene from such a stream goes through the laborious process of hydrogenating styrene and phenylacetylene to ethylbenzene, which then can be separated from a $C_8$ stream containing o-xylene, by azeotropic distillation with polar compounds such as low aliphatic acids, n-propanol, 1-nitropropane, or the like. The recovered ethylbenzene then is dehydrogenated back to styrene. Another process laboriously goes through an extractive distillation process employing such as dimethylformamide, or the like, to separate styrene from o-xylene and other close boiling aromatics.

Our process is simpler, effective, and highly useful. That this is true can be shown by the following calculated material balance:

Exemplification

In this example, 1000 lbs/hr (453.6 kg/hr) of a gasoline 1, obtained such as by pyrolysis of gas oil, is passed to fractionator 2 where the gasoline is fractionated under reduced pressures of such as about 440 mm Hg and at temperatures of such as about 60° C. to yield an overhead product 3, comprising benzene, toluene, mixed $C_5$ and $C_6$ paraffins, and olefins and diolefins, which is condensed 4, partially refluxed 5 as necessary, and the balance 6 sent to storge which can be later separated, if desired, into its components using conventional separating practices such as fractionation or the like.

The kettle product stream 7, now enriched in $C_8$–$C_{10}$ aromatic and olefinic compounds including styrene, is in part 8 reboiled 9 for recycle 11 as necessary, and the balance 12 passed to fractionator 13. A further fractionation is carried out 13 under reduced pressures of such as about 220 mm Hg and somewhat higher temperatures of such as about 100° C. to obtain an overhead product 14, which in part is cooled for recycle 16, and the remainder 17 of the primarily $C_8$ fraction comprising xylenes, ethylbenzene and styrene is passed to hydrogenation 24. The kettle product 18 comprising $C_9$–$C_{10}$ hydrocarbons is in part 19 reboiled 21 for recycle 22, and the remainder 23 is passed to storage and can be later separated, if desired, into its components.

Stream 16 is cooled 15 to such as about 40° C., the pressure is increased to atmospheric, and the cooled stream 17 is passed to hydrogenation reactor 24. Selective hydrogenation 24 of the phenylacetylene and $C_9$ dienes in the stream 17 can be accomplished in the presence of a stoichiometric amount of added hydrogen 26, employing a catalyst 27 typically of about 0.4 weight percent palladium on a calcium carbonate support partially deactivated with lead acetate to increase the selectivity of the reaction. Substantially all the phenylacetylene present in stream 17 is converted to styrene, whereas substantially all the $C_9$ dienes present are hydrogenated to monoolefins.

The effluent stream 28 from the hydrogenation step 24 is heated 29 to such as about 87° C. and passed 31 to contacting column 32. In column 32, operated under a reduced pressure of such as about 65 mm Hg, the styrene-containing stream 31 is contacted at a temperature of such as about 66° C. with a downwardly moving stream 71 comprising such as about 1 molar copper(I) dodecylbenzene sulfonate contained in a suitable solvent such as sec-butylbenzene. The overhead stream 33 comprises xylenes, toluene, and octanes, and is in part condensed 34 for recycle 35, while the remainder 36 is sent to storage and can be later separated, if desired, into its components by conventional means.

The kettle product stream 37, now at a temperature of such as about 92° C., can be in part 38 reboiled 39 to a temperature of such as about 100° C. for recycle 41, and the remainder 42 is passed to stripper column means 43 where it is contacted by an upwardly moving carbon monoxide stream 57 at a temperature of about 100° C. The amount of carbon monoxide used preferably is in the range of about 50% in excess of that required to react with the cuprous compound, thus displacing most effectively the more weakly attached styrene.

The overhead product stream 44 comprising styrene, nonenes, octenes, vinylcyclohexene, and excess carbon monoxide, is taken off at such as about 72° C. and 65 mm Hg, is cooled 44a and passed 44b to separation zone 50 where the liquid hydrocarbons 51 and carbon monoxide 54 are separated. The carbon monoxide stream 54, together with make-up CO 55 as needed is recycled 56 to column 43. The resulting liquid hydrocarbon stream 51 comprising styrene, nonenes, octenes, and vinyl cyclohexene, preferably in part is recycled 52 to contacting column 43, and the remainder 53 is passed to distillation column means 72 where the styrene and nonenes are separated from the octenes and vinylcyclohexene at such as about 70 mm Hg pressure.

The styrene-containing kettle product 77, which now is such as about 96.4 weight percent styrene, preferably is in part 78 reboiled 79 for recycle 81, and the remainder 82 is passed to storage zone 83 where it is cooled and the pressure allowed to reach atmospheric pressure. An inhibitor such as t-butylhydroquinone or the like can be added at this point, if desired, to retard polymerization of the stored monomer until needed 84.

Overhead stream 73 comprising octenes, vinylcyclohexene, and about 17 weight percent styrene, is cooled 74 and in part recycled 75, while the remainder is passed 76 to storage or to be further processed to separate the components as the situation warrants.

The bottom product stream 45, from stripper column means 43 comprising the copper(I) dodecylbenzene sulfonate-carbon monoxide complex contained in sec-butylbenzene usually in part 46 is reheated 47 to such as about 100° C. for recycle 48, and the remainder 49 is passed to stripper column means 58 maintained at atmospheric pressure and near such as about 183° C., the boiling point of the sec-butylbenzene, to effect decomplexing. The carbon monoxide leaves overhead 59 at such as about 173° C. at 760 mm Hg, and is cooled 61 for recycle 62 in part, and the balance 63 is combined with stream 56 to make stream 57 which is recycled to stripper column means 43. Any hydrocarbon carried over with stream 59 can be separated in a knockout zone, if desired (not shown).

The bottom product stream 64 from stripper column means 58 in part 65 is reboiled 66 to such as about 183° C. for recycle 67, and the remainder 68 is cooled 69, the pressure is reduced to such as about 65 mm Hg, and the stream 71 now at a temperature of such as about 66° C. is recycled 71 to absorber column means 32.

In an alternate embodiment, though presently less preferred, carbon monoxide is not used in the complexing-decomplexing zone. In this mode, the effluent stream 28 from the hydrogenation step 24 is heated 29 to such as about 87° C. and passed 91 to contacting column means 92. In contacting column means 92, operated under a reduced pressure of such as about 65 mm Hg, the styrene-containing stream 91 is contacted such as at a temperature of about 100° C. with a downwardly moving stream 105 of such as about 1 molar copper(I) dodecylbenzene sulfonate contained in a suitable solvent such as sec-butylbenzene. The overhead stream 93 at about 65 mm Hg and 66° C. comprises xylenes, toluene, and octanes, and is in part condensed 94 for recycle 95, while the remainder 96 is sent to storage and further separation as desired. The kettle product 97 copper(I) dodecylbenzene sulfonate styrene complex and sec-butylbenzene stream 97, now at about 100° C., from absorber column 92 is heated 98 and enters 99 stripper column means 101 at atmospheric pressure and a temperature of such as about 145° C., the boiling point of styrene. At these conditions, the complex is readily decomplexed. Overhead stream 109 at about 760 mm Hg and about 145° C. comprising styrene, nonenes, octenes and vinylcyclohexene is cooled 111 for partial recycle 113 and the balance 114 is passed to distillation column means 115 where the styrene and nonenes are separated as bottoms 122 from the octenes and vinylcyclohexene as overhead 116 at such as about 70 mm Hg pressure as described before. A portion 123 of the bottoms 122 preferably is reboiled 124 for recycle 125. The overhead 116 is cooled 117 and a portion preferably recycled 118, while the balance 119 is sent for storage and further separation as desired. The remainder of the bottoms 82 is handled as discussed hereinbefore.

What is claimed is:

1. A process for recovering styrene from a styrene-containing stream comprising styrene and other close-boiling hydrocarbons by the process which comprises:
   (a) extractively distilling said styrene-containing stream with an effective complex-forming amount of a copper(I) sulfonate salt in aromatic hydrocarbon solution effective to complex said styrene, thereby producing a copper(I) styrene sulfonate complex in aromatic hydrocarbon stream, and substantially stripping off said close-boiling hydrocarbons during said extractive distillation,
   (b) heating said copper (I) styrene sulfonate complex in aromatic hydrocarbon stream under thermal decomplexing conditions, thereby decomplexing said copper(I) styrene sulfonate complex and recovering said styrene as a styrene stream, and said copper(I) sulfonate as a solution in said aromatic hydrocarbon, and
   (c) recycling said copper(I) sulfonate in aromatic hydrocarbon solution from said heating step (b) to said extractively distilling step (a).

2. The process according to claim 1 wherein said extractively distilling step (a) employs a temperature in the range of about 0° to 120° C. and a pressure of about 40 to 760 mm Hg.

3. The process according to claim 2 wherein said extractively distilling step (a) employs a temperature in the range of about 20° C. to 100° C. and a pressure of about 65 to 700 mm Hg.

4. The process according to claim 2 wherein said heating step (b) thermal decomplexing of said copper(I) styrene sulfonate complex in aromatic hydrocarbon solution employs a temperature in the range of about 120° C. to 200° C. at a pressure of about 130 to 1100 mm Hg.

5. The process according to claim 4 employing a decomplexing temperature in the range of about 150° C. to 190° C. and a pressure in the range of about 320 to 890 mm Hg.

Table 1

| Stream No. | | | | | | Material Balance (lbs./hour) | | | | | | | | | | |
|---|---|---|---|---|---|---|---|---|---|---|---|---|---|---|---|---|
| Compound | 1 | 6 | 12 | 17 | 28 | 23 | 36 | 42 | 53 | 76 | 84 | 71 | 54 | 63 | 57 | 49 |
| pentanes, pentenes, pentadienes, cyclopentadiene | 45.8 | 45.8 | | | | | | | | | | | | | | |
| hexanes, hexenes, cyclohexane, hexadiene | 13.6 | 13.6 | | | | | | | | | | | | | | |
| methylcylclopentadiene, cyclohexadiene | 27.8 | 27.8 | | | | | | | | | | | | | | |
| benzene | 326.9 | 326.9 | | | | | | | | | | | | | | |
| heptanes, heptenes, heptadiene, dimethylcyclopentadiene | 29.1 | 29.1 | | | | | | | | | | | | | | |
| toluene | 210.0 | 208.0 | 2.0 | 2.0 | 2.0 | | 2.0 | | | | | | | | | |
| octanes | 27.1 | 23.8 | 3.3 | 3.3 | 3.3 | | 3.3 | | | | | | | | | |
| octenes | 13.8 | 12.1 | 1.7 | 1.7 | 1.7 | | | 1.7 | 1.7 | 1.7 | | | | | | |
| vinylcyclohexane | 13.3 | 11.5 | 1.8 | 1.8 | 1.8 | tr | | 1.8 | 1.8 | 1.8 | | | | | | |
| o-xylene | 23.4 | 1.2 | 22.2 | 21.7 | 21.7 | 0.53 | 21.7 | | | | | | | | | |
| m-xylene | 43.1 | 3.9 | 39.2 | 39.0 | 39.0 | 0.11 | 39.0 | | | | | | | | | |
| p-xylene | 18.5 | 1.7 | 16.8 | 16.8 | 16.8 | 0.05 | 16.8 | | | | | | | | | |
| ethylbenzene | 24.5 | 2.4 | 22.1 | 22.1 | 22.1 | 0.06 | 22.1 | | | | | | | | | |
| styrene | 69.5 | 2.5 | 67.0 | 64.5 | 65.7 | 2.52 | | 65.7 | 65.7 | 0.7 | 65.0 | | | | | |
| phenylacetylene, C$_9$ dienes | 4.3 | 0.5 | 3.8 | 3.66 | | 0.12 | | | | | | | | | | |
| nonenes | | | | | 2.42 | | | 2.42 | 2.42 | | 2.42 | | | | | |
| C$_3$ benzenes | 15.7 | 0.06 | 15.6 | 0.02 | 0.02 | 15.6 | 0.02 | | | | | | | | | |
| methylstyrene | 34.6 | 0.12 | 34.5 | 0.07 | 0.07 | 34.4 | 0.07 | | | | | | | | | |
| indene | 29.2 | | 29.2 | tr | tr | 29.4 | tr | tr | | | | | | | | |
| C$_4$ benzenes | 2.3 | | 2.3 | | | 2.29 | | | | | | | | | | |
| dicyclopentadiene, dimethylstyrene | 27.5 | | 27.5 | | | 27.5 | | | | | | | | | | |
| copper(I) dodecylbenezene sulfonate | | | | | | | | 240.6 | | | | 240.6 | | | | 240.6 |
| C$_{10}$ aromatics | | | | | | | | 325.9 | | | | 325.9 | | | | 325.9 |
| CO | | | | | | | | | | | | | 9.5 | 19.1 | 28.6 | 19.08 |
| totals | 1000.0 | 710.9 | 289.0 | 176.7 | 176.7 | 112.6 | 105.0 | 638.1 | 71.6 | 4.2 | 67.4 | 566.5 | 9.5 | 19.1 | 28.6 | 585.6 |

The disclosure, including data, has illustrated the value and effectiveness of our invention. The examples, knowledge and background of the field of the invention, and of general principles of chemistry and engineering, have formed the bases from which the broad descriptions of our invention, including the ranges of conditions and generic groups of operant components have been developed, and have formed the bases for our claims here appended.

6. The process according to claim 2 employing said copper(I) sulfonate in said contacting step (a) as a concentration of about 0.2 to 2.5 molar solution in said aromatic hydrocarbon.

7. The process according to claim 6 employing said copper(I) sulfonate as a concentration of about 0.5 to 2 molar solution in said aromatic hydrocarbon.

8. The process according to claim 6 wherein said copper(I) sulfonate complex in an aromatic hydrocarbon employs, as said aromatic hydrocarbon, n-propylbenzene, sec-butylbenzene, amylbenzene, or mixture of alkylbenzenes, wherein the boiling point of said aromatic solvent at atmospheric pressure is at least about 145° C.

9. The process according to claim 1 wherein said copper(I) sulfonate is:
  (1) the copper(I) salt of an alkane sulfonic acid of 4 to 20 carbon atoms per molecule,
  (2) the copper(I) salt of an aromatic sulfonic acid of 6 to 22 carbon atoms per molecule, or
  (3) the copper(I) salt of a petroleum sulfonic acid.

10. The process according to claim 9 wherein said copper(I) sulfonate is said (1) copper(I) salt of an alkane sulfonic acid of 4 to 20 carbon atoms per molecule and is selected from the group consisting of n-butane sulfonic acid, 2-ethylhexane sulfonic acid, 2-methylnonane sulfonic acid, dodecane sulfonic acid, 2-ethyl-5-n-octyldecane sulfonic acid, n-eicosane sulfonic acid, or admixture thereof.

11. The process according to claim 10 wherein said (1) alkane sulfonic acid is 2-ethyl-1-hexane sulfonic acid.

12. The process according to claim 9 wherein said copper(I) sulfonate is said (2) copper(I) salt of an aromatic sulfonic acid of 6 to 22 carbon atoms per molecule, and is selected from the group consisting of benzene sulfonic acid, p-toluene sulfonic acid, p-dodecylbenzene sulfonic acid, p-hexadecylbenzene sulfonic acid, phenol sulfonic acid, napthol sulfonic acid, p-chlorobenzene sulfonic acid, p-bromobenzene sulfonic acid, or admixture thereof.

13. The process according to claim 9, wherein said copper(I) sulfonate is said (3) copper(I) salt of a petroleum sulfonic acid.

14. The process according to claim 4 wherein said styrene-containing stream is a 137°–147° C. boiling fraction cut from a refinery naphtha stream.

15. The process according to claim 14 wherein said copper(I) sulfonate is copper(I) dodecylbenzene sulfonate, and said aromatic hydrocarbon solvent is sec-butylbenzene.

16. A process for separating styrene from a $C_8+$ stream comprising styrene and other close-boiling components thereof, which comprises the steps of:
  (a) extractively distilling said $C_8+$ stream with an effective amount of a copper(I) sulfonate salt in aromatic hydrocrbon solution, thereby extracting styrene as a copper(I) styrene sulfonate complex in aromatic hydrocarbon solution, while substantially stripping off said close-boiling components,
  (b) heating said copper(I) styrene sulfonate complex in aromatic hydrocarbon solution, thereby separating said styrene from said complex as a styrene stream, and said copper(I) sulfonate as a solution in said aromatic solvent, and
  (c) recycling said copper(I) sulfonate in aromatic hydrocarbon from said step (b) to said extractively distilling step (a).

17. The process for recovering styrene from a $C_5+$ stream derived from cracking of naphtha, which comprises:
  fractionating said $C_5+$ stream to obtain a stream comprising saturated and unsaturated hydrocarbons of about 5 to 7 carbon atoms per molecule, and a $C_8+$ stream,
  fractionating said $C_8+$ stream to obtain a boiling fraction of about 137° to 147° C. comprising close-boiling aromatic hydrocarbons, diolefins, paraffins, naphthenes, acetylenes, and styrene,
  hydrogenating said 137°–147° C. boiling fraction to convert diolefins and acetylenics to more saturated compounds,
  extractively distilling the resulting hydrogenated fraction with an effective amount of a solution of a copper(I) sulfonate in an aromatic hydrocarbon solvent, thereby complexing said styrene with said copper(I) sulfonate as a copper(I) styrene sulfonate complex in aromatic solvent, while substantially stripping off noncomplexed components,
  decomplexing said styrene from said copper(I) styrene sulfonate complex in aromatic solvent under solution decomplexing conditions effective to recover a styrene stream and a copper(I) sulfonate in aromatic hydrocarbon stream for recycle, and
  recycling said copper(I) sulfonate in aromatic hydrocarbon stream to said extractively distilling step.

18. The process according to claim 17 wherein said decomplexing step is a thermal decomposition step wherein said copper(I) styrene sulfonate complex solution in aromatic hydrocarbon is heated to a temperature whereby said styrene is recovered, and said copper(I) sulfonate and aromatic hydrocarbon are recovered and recycled.

19. The process according to claim 18 wherein said decomplexing step comprises treating said copper(I) styrene sulfonate complex in aromatic hydrocarbon complex with carbon monoxide under conditions effective to displace said styrene and produce a copper(I) carbon monoxide sulfonate complex in aromatic hydrocarbon,
  and thereafter decomposing said copper(I) carbon monoxide sulfonate complex in aromatic hydrocrbon under thermal decomposition conditions effective to recover said carbon monoxide for recycle, and said copper(I) sulfonate in aromatic hydrocarbon for recycle.

20. The process for recovering styrene from a styrene-containing stream comprising styrene and other close-boiling hydrocarbons by the process which comprises:
  (a) contacting said styrene-containing stream with an effective amount of a copper(I) sulfonate salt aromatic hydrocarbon solution to effectuate complexing of said styrene under reaction conditions effective to complex said styrene, thereby producing a copper(I) styrene sulfonate complex in aromatic hydrocarbon solution,
  (b) displacing said styrene from said copper(I) styrene sulfonate complex in aromatic hydrocarbon solution with an effective amount of carbon monoxide at temperatures and pressures effective to result in a styrene stream, and a copper(I) carbon monoxide sulfonate complex in aromatic solvent,
  (c) thermally decomplexing said copper(1) carbon monoxide sulfonate complex in aromatic hydrocarbon solution to recover a carbon monoxide stream and a copper(I) sulfonate in aromatic hydrocarbon stream, (d) recycling said carbon monoxide to said displacing step (b), and (e) recycling said copper(I) sulfonate in aromatic solvent to said contacting step (a).

21. The process according to claim 20 wherein said displacing step (b) employs temperatures of about 0° to 110° C. and pressures of about 20 to 1500 mm Hg.

22. The process according to claim 21 wherein said displacing step (b) employs temperatures of about 20° to 100° C. and pressures of about 65 to 760 mm Hg.

23. The process of claim 20 employing in said step (a) a temperature in the range of about 0° C. to 120° C. and a pressure in the range of about 40 to 760 mm Hg.

24. A process for separating styrene from a $C_8+$ stream comprising styrene and other close-boiling components, which comprises the steps of:

(a) contacting said $C_8+$ stream with a copper(I) sulfonate salt employing effective amounts and conditions to thereby extract styrene as a copper(I) styrene sulfonate complex, (b) separating said styrene from said copper(I) styrene sulfonate complex by treating said copper(I) styrene sulfonate complex with carbon monoxide under conditions effective to release such styrene and produce a copper(I) carbon monoxide sulfonate complex, and thereafter decomposing said copper(I) carbon monoxide sulfonate complex under thermal decomposition conditions to recover said carbon monoxide for recycle, and said copper(I) sulfonate for recycle, thereby producing a stream of substantially pure styrene.

* * * * *